United States Patent [19]

Clark, Jr.

[11] Patent Number: 5,344,396
[45] Date of Patent: Sep. 6, 1994

[54] DEVICE FOR STRETCHING THE FORESKIN OF THE PENIS

[76] Inventor: Roland T. Clark, Jr., 22052 Islander La., Huntington Beach, Calif. 92646

[21] Appl. No.: 929,814

[22] Filed: Aug. 13, 1992

[51] Int. Cl.$^5$ .............................. A61F 5/00
[52] U.S. Cl. .............................. 600/38
[58] Field of Search ............ 600/38; 604/326, 171, 604/270, 327, 346, 347, 349–352, 355; 606/118

[56] References Cited

U.S. PATENT DOCUMENTS

| | | | |
|---|---|---|---|
| 480,911 | 8/1892 | Vance | 604/349 |
| 1,026,481 | 5/1912 | Ward | 128/60 |
| 2,586,674 | 2/1952 | Lönne | 604/349 X |
| 4,388,923 | 6/1983 | Heimreid | 604/352 |
| 4,419,097 | 12/1983 | Rowland | 604/352 |
| 4,626,250 | 12/1986 | Schneider | 604/352 |
| 4,640,688 | 2/1987 | Hauser | 604/352 |
| 4,769,020 | 9/1988 | Eaton | 604/352 |
| 4,820,290 | 4/1989 | Yahr | 604/352 X |
| 4,821,742 | 4/1989 | Phelps, III | 604/352 X |
| 4,846,909 | 7/1989 | Klug et al. | 604/352 X |
| 5,084,037 | 1/1992 | Barnett | 604/350 X |

OTHER PUBLICATIONS

Photocopy of brochure for Wayne Griffiths' "Foreballs" product, Wayne Griffiths, Concord, Calif.

*Primary Examiner*—Robert A. Hafer
*Assistant Examiner*—Brian E. Hanlon
*Attorney, Agent, or Firm*—Macro-Search Corp.

[57] ABSTRACT

An apparatus is provided for stretching a circumcised foreskin of a penis. A tubular body provides an outer surface. An indented portion is included at one end of the body for accepting the tip of the penis, and a passage within the body interconnects the indented portion at the one end of the body with the other end of the body. In operation, with the tip of the penis inserted into the indented portion, and the foreskin drawn toward the tip to contact the outer surface for removable attachment thereto. The weight of the body exerts a tension force within the foreskin to stretch the foreskin. Additional weights may be attached at the other end of the body. In an alternate embodiment of the invention, the body is comprised of an outer portion including the outer surface, and an inner portion including the indented portion. The inner portion is slidably and axially engaged within the outer portion. A spring enclosed within the inner portion and the outer portion urges the portions apart in mutual linear translation. With the foreskin attached to the outer surface, and the tip of the penis inserted into the indented portion, such translation places a tension force within the foreskin for stretching the foreskin. In such an alternate embodiment of the invention, the passage may be a flexible tube, a coiled tube, or a telescoping tube.

5 Claims, 2 Drawing Sheets

DEVICE FOR STRETCHING THE FORESKIN OF THE PENIS

FIELD OF THE INVENTION

This invention relates generally to stretching devices, and, more particularly, is directed toward a device for stretching the foreskin of a penis.

BACKGROUND OF THE INVENTION

Many advantages of circumcision have been cited over the years, and heretofore it has been a commonly held belief that circumcision has no disadvantageous effects. This is evidenced by the large number of male infants that undergo this procedure shortly after birth. However, some men have found themselves harbouring resentment at having such a procedure forced upon them without their consent or understanding at such an early age. Further, some men come to feel that circumcision is a disfigurement, and that, having undergone circumcision, they have been permenantly marred and are not whole or natural. Further, recent medical reports have indicated that circumcision results in an eventual decrease of sensitivity of the tip of the penis, or glans penis. For these reasons, many circumcised men have attempted to re-gain their foreskins, either through surgery or by stretching any remaining portion of foreskin towards the tip of the penis over a period of time. Such stretching can be accomplished typically within several months when a consistant stretching force is applied. Moreover, such stretching is permanent and results in a stretched foreskin that closely simulates an intact, original foreskin. Once a stretched or surgically attached foreskin has been restored, such men have experienced an increase in sensitivity and an overall increase in sexual enjoyment. Moreover, many men experience great psychological benefit by knowing that their foreskin has been restored.

Clear disadvantages are evident with the surgical method of foreskin restoration. Surgical technique requires cutting the skin, which then must heal. Not only does such a process cause discomfort, the possibility for infection is always prominent with any surgical procedure. Further, surgergy is dearly an expensive solution. However, there is also a distinct lack of prior art devices suitable for stretching or elongating the remaining foreskin of a circumcised penis in a gradual manner. One such device is a small dumb-bell shaped weight that is taped to the foreskin. The weight of the device, worn daily over a period of weeks or months, stretches the foreskin towards the tip of the penis. However, while using such a device the tip of the penis is forced into the convex surface of the spherical weight, causing discomfort and potential blood circulation problems. Moreover, when the user of such a device needs to urinate, the device must be completely removed. This is inconvenient and frequently results in non-use. Yet such a device must be used repeatidly over a period of several months for such a device to be effective. A further drawback of such a device is that its weight is not adjustable. Some men find the weight of such a device painfully uncomfortable, yet others find that the weight is insufficient to produce results fast enough.

Clearly, then, there is a need for a comfortable, easy-to-use, non-surgical foreskin stretching device. Such a needed device would allow the user to urinate without having to remove the device, and would properly shape the stretched foreskin into a natural, sheath-like truncated cone around the tip of the penis. Such a needed device would allow the stretching force to be adjustable, and could be easily removed if necessary. Moreover, such a needed device would be unobtrusive, allowing the user to wear such a device during the course of the day without attracting undo attention and without experiencing pain. Such a needed device would further be inexpensive, easy to use, and easy to clean. The present invention fulfills these needs and provides further related advantages.

SUMMARY OF THE INVENTION

The present invention is a device for stretching a circumcised foreskin of a penis. A tubular body provides an outer surface. An indented portion is included at one end of the body for accepting the tip of the penis, and a passage within the body interconnects the indented portion at the one end of the body with the other end of the body.

In operation, with the tip of the penis inserted into the indented portion, and the foreskin drawn toward the tip to contact the outer surface for removable attachment thereto. The weight of the body exerts a tension force within the foreskin to stretch the foreskin. A weight attachment means may be additionally included at the other end of the body. The passage is included for carrying urine from the tip to the other end of the body, where it is discharged from the body.

In an alternate embodiment of the invention, the body is comprised of an outer portion including the outer surface, and an inner portion including the indented portion. The inner portion is slidably and axially engaged within the outer portion. A spring enclosed within the inner portion and the outer portion urges the portions apart in mutual linear translation. With the foreskin attached to the outer surface, and the tip of the penis inserted into the indented portion, such translation places a tension force within the foreskin for stretching the foreskin. In such an alternate embodiment of the invention, the passage may be a flexible tube, a coiled tube, or a telescoping tube.

The present invention is a comfortable, easy-to-use, non-surgical foreskin stretching device. The present invention allows the user to urinate without having to remove the device, and properly shapes the stretched foreskin into a natural, sheath-like truncated cone around the tip of the penis. The present invention allows the stretching force to be adjustable, and can be easily removed from the penis if necessary. Moreover, the present device is unobtrusive, allowing the user to wear such the device during the course of the day without attracting undo attention and without experiencing pain. The present invention is inexpensive, easy to use, and easy to clean. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
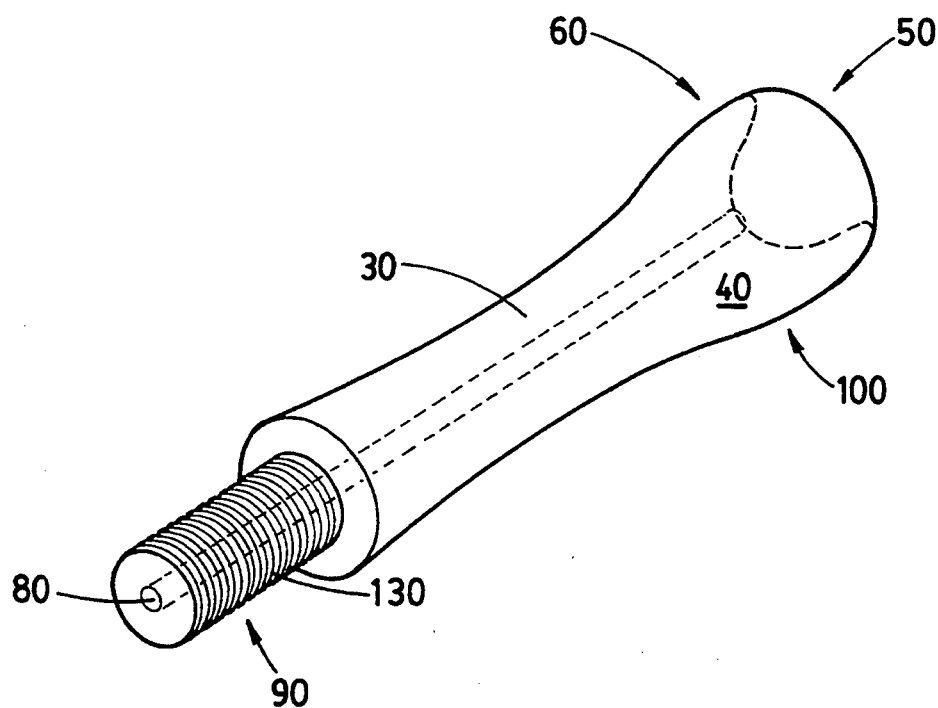
FIG. 1 is a perspective illustration of the invention, illustrating a body and a threaded stud portion thereof.
Figure 2:
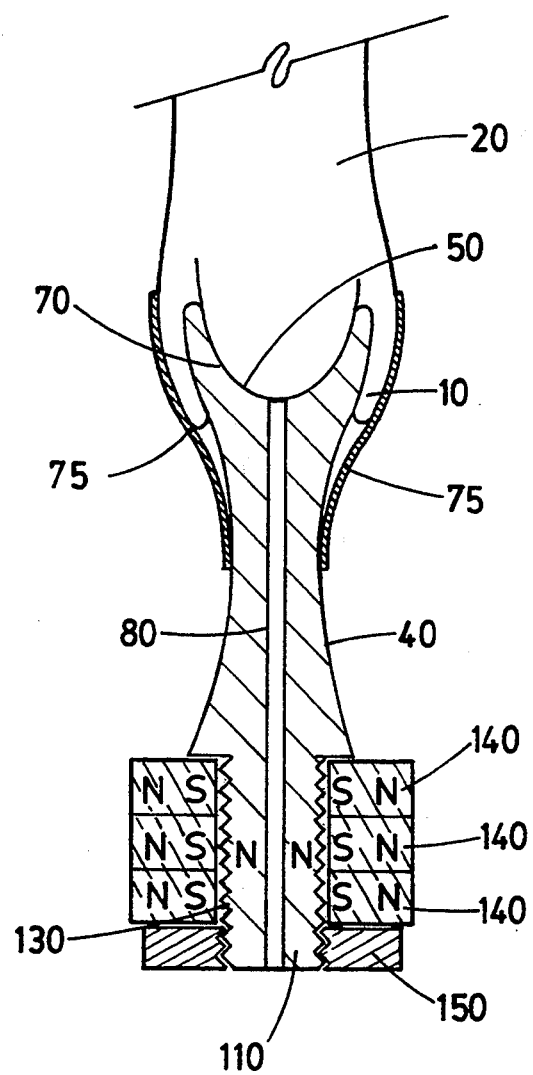
FIG. 2 is a cross-sectional view of the invention, illustrating a passage through the body and a weight attachment means of the invention.
Figure 6:
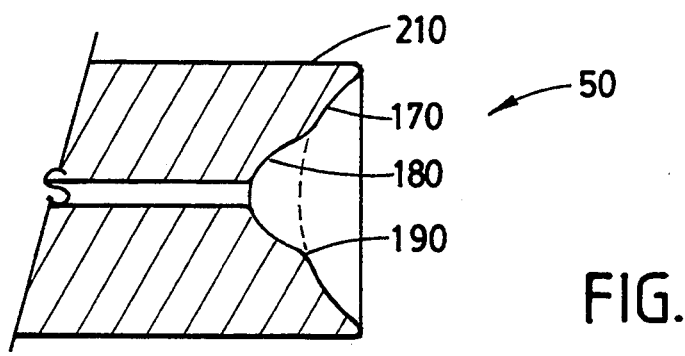
FIG. 6 is a partial cross-sectional view of the invention, illustrating an outer portion and an inner portion forming a sealing circular lip.

FIGS. 1 and 2 show a device for stretching a circumcised foreskin 10 of a penis 20. A tubular body 30 provides an outer surface 40. An indented portion 50 is included at one end 60 of the body 30 for accepting the tip 70 of the penis, and a passage 80 within the body 30 interconnects the indented portion 50 at the one end 60 of the body 30 with the other end 90 of the body 30. Preferably, a medial portion 100 of the outer surface 40 is tapered so as to hold the foreskin 10 in contact with the medial portion 100 in such a way as that the foreskin 10 takes the shape of a truncated cone. Preferably, the indented portion 50 is a concave smooth surface 160 approximating the shape of the tip 70 of the penis 20. The smooth surface 160 may include an second spherical area 170 and an first spherical area 180, the areas 170,180 being joined by a circular lip 190 (FIG. 6). The lip 190 forms a water-tight seal against the tip 70 of the penis 20. The body 30 may be manufactured from polished metal or smooth plastic.

In operation, the tip 70 of the penis 20 is inserted into the indented portion 50, and the foreskin 10 is drawn toward the tip 70 to contact the outer surface 40 for removable attachment thereto. Preferably, tape 75, such as surgical tape, is used to secure the foreskin 10 to the outer surface 40 (FIG. 1). Alternately, a condom may be rolled over the device to hold the foreskin 10 to the outer surface 40 (not shown). The weight of the body 30 exerts a tension force within the foreskin 10 to stretch the foreskin 10. The passage 80 is included for carrying urine from the tip 70 to the other end 90 of the body 30, where it is discharged from the body 30. Manufacturing the body 30 from polished metal is preferably, since the body 30 must have sufficient weight to stretch the foreskin 10.

A weight attachment means 110 may be additionally included at the other end 90 of the body 30. Such a weight attachment means 110 could include one or more weights 140 for removable engagement with the weight attachment means 110. As such, the tension force in the foreskin 10 may be increased by attaching weights 140, and may be decreased by removing weights 140. In one embodiment of the invention, the weight attachment means 110 is a screw threaded stud portion 130 positioned coaxial with the passage 80. Each of the weights 140 is a plain washer that slidably fits over the stud portion 130. A locking nut 150 is included for engagement with the stud portion 130 so as to capture each weight 140 on the body 30. In another embodiment of the invention, also illustrated in FIG. 2, the weight attachment means 110 employs magnetic attraction between each weight 120, preferably a soft iron washer, and the body 30, which includes a magnet, for holding the weights 140 to the body 30. In such an embodiment a locking nut 150 is unnecessary. Clearly, other weight attachment means 110 could be readily devised by one skilled in the art.

Figure 3:
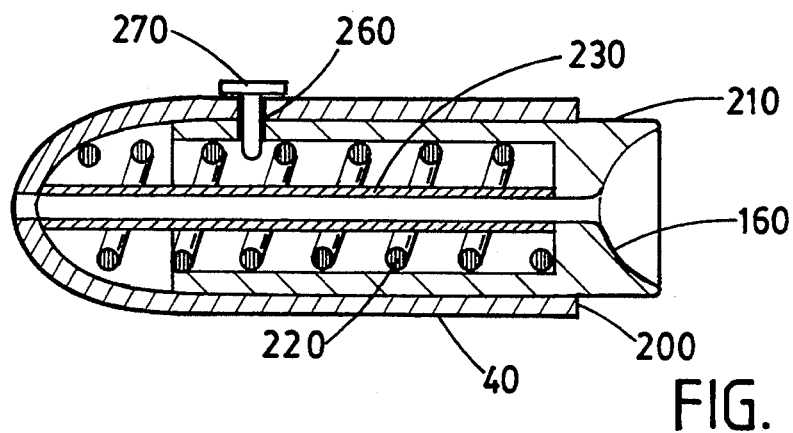
FIG. 3 is a cross-sectional view of an alternate embodiment of the invention, illustrating an inner and an outer portion slidably engaged and urged apart by a spring.
Figure 4:
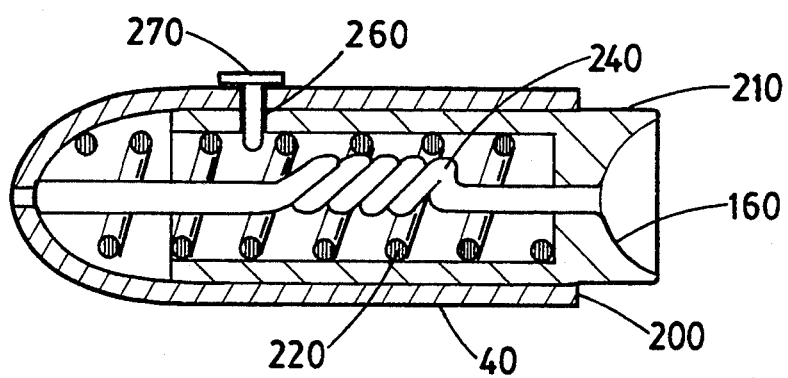
FIG. 4 is a partial cross-sectional view of the invention, illustrating a coiled tube passage.
Figure 5:
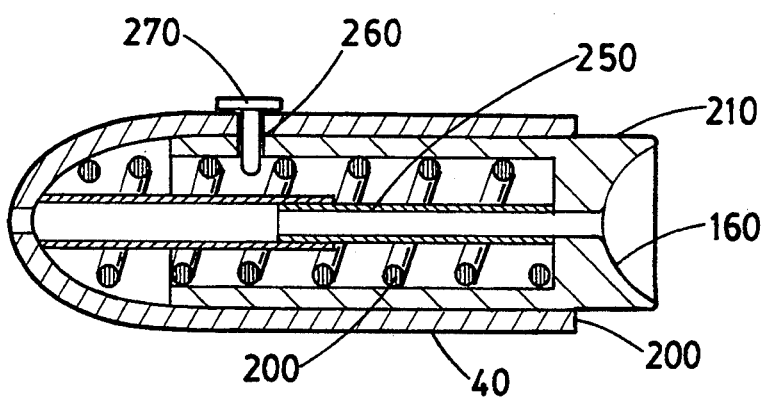
FIG. 5 is a partial cross-sectional view of the invention, illustrating a telescoping tube passage.

In an alternate embodiment of the invention, the body 30 is comprised of an outer portion 200 including the outer surface 40, and an inner portion 210 including the concave smooth surface 160 (FIG. 3). The inner portion 210 is slidably and axially engaged within the outer portion 200. A spring means 220 enclosed within the inner portion 210 and the outer portion 200 urges the portions 200,210 apart in opposed linear translation. With the foreskin 10 attached to the outer surface 40, and the tip 70 of the penis 20 inserted into the concave smooth surface 160, such translation places a tension force within the foreskin 10 for stretching the foreskin 40. Preferably, the outer portion 200 and the inner portion 210 each define a clearance hole 260 therein. The clearance holes 260 each are in alignment when the portions 200,210 are fully engaged. A locking pin 270 for insertion into the holes 260 holds the portions in full engagement (FIG. 3), such that the tension force for stretching the foreskin 10 may be temporarily relaxed without needing to remove the device from the penis 20. In such an alternate embodiment of the invention, the passage 80 may be a flexible tube 230 (FIG. 3), a coiled tube 240 (FIG. 4), or a telescoping tube 250 (FIG. 5), such that when the outer portion 200 slides away from the inner portion 210 the passage 80 will lengthen accordingly. Clearly, other passages 80 could be readily devised by one skilled in the art.

While the invention has been described with reference to a preferred embodiment, it is to be clearly understood by those skilled in the art that the invention is not limited thereto. Rather, the scope of the invention is to be interpreted only in conjunction with the appended claims.

What is claimed is:

1. A device for stretching a circumcised foreskin of a penis comprising, a tubular body providing an outer surface, an indented portion at one end of the body for accepting the tip of the penis, and a passage within the body interconnecting the indented portion at one end of the body with the other end of the body, so that with the tip of the penis inserted into the indented portion, and the foreskin drawn toward the tip to contact the outer surface for removable attachment thereto the weight of the body exerts a tension force within the foreskin to stretch the foreskin, the passage carrying urine from the tip to be discharged at the other end of the body, wherein the body is comprised of an outer portion including the outer surface and an inner portion including the indented portion, the inner portion being slidably, axially engaged within the outer portion, and a spring means enclosed within the inner and outer portions for urging said portions apart in opposed linear translation such that with the foreskin attached to the outer surface, and the tip inserted into the indented portion, said translation places a tension force within the foreskin, said force tending to stretch the foreskin.

2. The device of claim 1 wherein the passage is a flexible tube.

3. The device of claim 1 wherein the passage is a coiled tube.

4. The device of claim 1 wherein the passage is a telescoping tube.

5. The device of claim 1 wherein the outer and inner portions each define a clearance hole therein, said clearance holes being in alignment when the portions are fully engaged, and further including a locking pin for insertion into said holes for holding the portions in full engagement.

* * * * *